United States Patent [19]

van de Moesdijk

[11] 4,328,198
[45] May 4, 1982

[54] CYCLIC PROCESS FOR THE PREPARATION AND PROCESSING OF A HYDROXYLAMMONIUM SALT SOLUTION

[75] Inventor: Cornelis G. M. van de Moesdijk, Elsloo, Netherlands

[73] Assignee: Stamicarbon, B.V., Geleen, Netherlands

[21] Appl. No.: 193,107

[22] Filed: Oct. 2, 1980

[30] Foreign Application Priority Data

Oct. 5, 1979 [NL] Netherlands .......................... 7907395

[51] Int. Cl.$^3$ ................................................ C01C 3/08
[52] U.S. Cl. ...................................... 423/371; 564/259
[58] Field of Search ......................... 423/371; 564/259

[56] References Cited

U.S. PATENT DOCUMENTS 3,641,150 2/1972 de Roolj .............................. 564/259
4,122,153 10/1978 Haasen et al. ....................... 564/259

OTHER PUBLICATIONS

Perry, *Chemical Engineers' Handbook*, McGraw-Hill Book Co., Inc., Third Edition (1950), p. 456.

*Primary Examiner*—O. R. Vertiz
*Assistant Examiner*—Wayne A. Langel
*Attorney, Agent, or Firm*—Cushman, Darby & Cushman

[57] ABSTRACT

The process relates to hydroxylammonium salts.

Cyclic process for the preparation and processing of a hydroxylammonium salt solution, in which an aqueous acid reaction medium is kept in circulation between a hydroxylammonium salt synthesis zone and an oxime synthesis zone, and in which the circulating liquid is continuously supplied with nitrogen monoxide, which serves as nitrogen source for the formation of the hydroxylammonium salt, and which is converted into hydroxylamine by catalytic reduction with hydrogen.

The circulating liquid is, before it enters the hydroxylammonium salt synthesis zone, subjected to a stripping process by bringing the circulating liquid via a heat-exchanging surface in heat-exchange with nitrogen monoxide containing water vapor, upon which the water vapor condenses, and the remaining gas containing nitrogen monoxide as nitrogen source is used in the reduction of nitrogen monoxide to hydroxylamine.

2 Claims, No Drawings

CYCLIC PROCESS FOR THE PREPARATION AND PROCESSING OF A HYDROXYLAMMONIUM SALT SOLUTION

The invention relates to a cyclic process for the preparation and processing of a hydroxylammonium salt solution in which an aqueous acid reaction medium is kept in circulation between a hydroxylammonium salt synthesis zone and an oxime synthesis zone and in which the circulating liquid is continuously supplied with nitrogen monoxide, which serves as nitrogen source for the formation of the hydroxylammonium salt, and which is converted to hydroxylamine by catalytic reaction with hydrogen, for instance as described in the American patent specification No. 3,641,150.

As is known, an important application of hydroxylammonium salts is the preparation of oximes from ketones or aldehydes in particular the preparation of cyclohexanone oxime from cyclohexanone.

In said cyclic process a hydrogenation catalyst, for instance platinum on carbon, graphite or aluminum oxide, is used for the reduction of the nitrogen monoxide, and optionally a promoter such as compounds of the elements S, Se, Te and Bi.

It has now been found that the activity of the catalyst is adversely affected if the catalyst is contacted with organic substances, for instance the carbonyl compound to be converted and the oxime formed from this. If catalyst poisoning is to be prevented, it is, therefore, essential that the circulating reaction medium, before it enters the hydroxylamine synthesis zone, is freed as much as possible from organic compounds dissolved in it. The present invention provides a suitable method to achieve this goal.

The cyclic process according to the invention for the preparation and processing of a hydroxylammonium salt solution, in which an aqueous acid reaction medium is kept in circulation between a hydroxylammonium salt synthesis zone and an oxime synthesis zone, and in which the circulating liquid is continuously supplied with nitrogen monoxide, which serves as nitrogen source for the formation of the hydroxylammonium salt, and which is converted into hydroxylamine by catalytic reduction with hydrogen, is characterized in that the circulation liquid is, before it enters the hydroxylammonium salt synthesis zone, subjected to a stripping process by bringing the circulating liquid via a heat-exchanging surface in heat-exchange with nitrogen monoxide containing water vapour, upon which the water vapour condenses, and the remaining gas containing nitrogen monoxide as nitrogen source is used in the reduction of nitrogen monoxide to hydroxylamine.

The nitrogen monoxide containing water vapour to be used for said heat-exchange according to the present invention can be obtained in a known way by combustion of ammonia with oxygen and/or air over a platinum catalyst in the presence of steam and removal of the oxygen and/or nitrogen dioxide present in the combustion gases, for instance in the way described in the Britisch patent specifications Nos. 916,693 and 1,186,408. An advantage of the heat-exchange according to the present invention is that one apparatus can be used for two purposes, viz. removal of catalyst poison from the circulating liquid and of water vapour from the nitrogen monoxide containing water vapour.

The temperature of the nitrogen monoxide containing water vapour to be used can be varied. By preference a temperature of 100°–450° C. is used. The heat exchange is preferably carried out so that after heat-exchange and condensation of water vapour a gas containing nitrogen monoxide having a temperature of 60°–200° C. can be obtained which is suitable for the reduction to hydroxylamine.

In the reduction of the nitrogen monoxide in most cases a slight amount of ammonia is formed besides the hydroxylamine. To prevent the circulating liquid from becoming ever richer in ammonia, ammonia is to be discharged, for instance by periodically or continuously removing ammonium salt from part of the circulating liquid by crystallization. By preference, a portion of the circulating liquid is continuously or periodically contacted with nitrogen monoxide containing nitrogen dioxide under such conditions that the ammonium ions are broken down to nitrogen in the way described in the American patent specification No. 3,641,150. The nitrogen monoxide containing nitrogen dioxide that is required for this can be obtained by mixing a portion of the nitrogen monoxide containing water vapour that is to be used for the heat exchange with some air.

The invention will be further elucidated in the following example.

EXAMPLE

A circulating liquid discharged form a cyclohexanone oxime synthesis zone is passed through a stripping column which contains a heating spiral through which nitrogen monoxide containing water vapour is passed. The circulating liquid is led to the top of the column at a temperature of 100° C. and is discharged from the bottom of the column at a temperature of approximately 110° C. The discharged circulating liquid is then cooled to 50° C. by heat exchange with the circulating liquid to be supplied to the column, and is next led to a hydroxylammonium salt synthesis zone. The circulating liquid contains per kilogram 0.05 moles of monohydroxylammonium phosphate, 0.8 moles of monoammonium phosphate and 1.85 moles of phosphoric acid.

The nitrogen containing water vapour is supplied to the heating spiral at a temperature of 363° C. and is discharged from this spiral at a temperature of 122° C. The nitrogen monoxide supplied is of the following composition: 13 vol.% of NO, 1.5 vol.% of $N_2$, less than 0.1 vol.% of $HNO_3$ and 85.1 vol.% of water vapour. As a result of the heat exchange a large amount of water vapour condenses. After the heat exchange, the nitrogen monoxide is of the following composition: 67.1 vol.% of NO, 6.85 vol.% of $N_2$, less than 0.1 vol.% of $HNO_3$ and 26.1 vol.% of water vapour. This nitrogen monoxide is, after cooling to 50° C., passed to the hydroxylammonium salt synthesis zone, where it is reduced with hydrogen in a known way.

For proper stripping, per kilogram of circulating liquid, 0.023 kilograms of water are supplied to the stripping column. From the stripping column 0.071 kilograms of water vapour, in which the stripped organic contaminants are contained, are discharged per kilogram of circulating liquid. This amount of water vapour agrees with the amount that is to be discharged to keep the water content of the circulating liquid constant and is made up of the amount of water supplied to the stripping column and the amount of water formed in the oximation.

The size of the required heat-exchanging surface of the heating spiral in the stripping column is as a matter of course dependent upon the amount of the circulating liquid to be processed. The conditions mentioned above can be achieved when processing 5.5 kilograms of circulating liquid an hour with a heat-exchanging surface of the spiral of 0.03 m² and a supply of 0.127 kilograms of nitrogen monoxide an hour in the nitrogen monoxide containing water vapour.

What is claimed is:

1. In cyclic processes for the preparation and processing of a hydroxylammonium salt solution in which a circulating aqueous acid reaction medium is maintained in circulation between a hydroxylammonium salt synthesis zone and an oxime synthesis zone wherein the said reaction medium is continuously supplied with nitrogen monoxide as a nitrogen source for the formation of the said hydroxylammonium salt by catalytic reduction to hydroxylamine by means of hydrogen, the improvement which in combination with said process consists essentially in subjecting said circulating aqueous reaction medium to a stripping process, to remove organic catalyst poison contaminants therefrom, before re-circulating said medium to said hydroxylammonium salt synthesis zone, by inducing an indirect heat-exchange between said aqueous reaction medium and water-vapor-containing nitrogen monoxide gas stream, to cause discharge of water vapor from said aqueous medium with entrainment of said organic contaminants leaving an aqueous acid reaction medium for circulation substantially free from said poisons while simultaneously causing condensation of at least a portion of the water vapor from said gas stream to condense on the heat-exchange surface, thereby forming a substantially de-watered nitrogen monoxide gas for use as said nitrogen source.

2. A process according to claim 1 wherein said water vapor containing nitrogen monoxide has a temperature between 100° C. and 450° C.

* * * * *